United States Patent
Forbes et al.

(10) Patent No.: US 6,265,408 B1
(45) Date of Patent: Jul. 24, 2001

(54) SULPHONAMIDE DERIVATIVES AND THEIR USE IN THE TREATMENT OF CNS DISORDERS

(75) Inventors: Ian Thomson Forbes, Stevenage; Francis David King, Bishops Stortford; Shirley Katherine Rahman, Bishop's Stortford, all of (GB)

(73) Assignee: SmithKline Beecham plc, Brentford (GB)

(*) Notice: Subject to any disclaimer, the term of this patent is extended or adjusted under 35 U.S.C. 154(b) by 0 days.

(21) Appl. No.: 09/202,776

(22) PCT Filed: Jun. 17, 1997

(86) PCT No.: PCT/EP97/03159

§ 371 Date: Mar. 5, 1999

§ 102(e) Date: Mar. 5, 1999

(87) PCT Pub. No.: WO97/48681

PCT Pub. Date: Dec. 24, 1997

(30) Foreign Application Priority Data

Jun. 20, 1996 (GB) .................................................. 9612884

(51) Int. Cl.[7] .................. A61K 31/496; A61K 31/4453; C07D 401/06; C07D 403/06

(52) U.S. Cl. .................. 514/254.01; 514/326; 514/227.8; 514/235.5; 514/252.05; 514/316; 514/217.04; 540/597; 544/360; 544/372; 544/58.5; 544/141; 544/238; 544/364; 546/208; 546/187; 546/191; 546/146; 546/149; 546/172; 546/112; 546/125

(58) Field of Search .......................... 546/208; 544/58.5, 544/141, 372, 238; 514/252, 326, 227.8, 235.5, 254.01

(56) References Cited

FOREIGN PATENT DOCUMENTS

| 0 021 580 | 1/1981 | (EP) . |
|---|---|---|
| 0 076 072 | 4/1983 | (EP) . |
| 0361 791 | 4/1990 | (EP) . |
| WO 96 33172 | 10/1996 | (WO) . |

OTHER PUBLICATIONS

Mullins et al., Medline Abstract for *Neuropsychopharmacology* 21, p. 352–367 (1999).*
Healy et al., Medline Abstract for *Neuropsychopharmacology* 21, p. 341–351, (1999).*
Hendrie et al., *Tetrahedron*, vol. 43, No. 14, p. 3289–3294 (1987).*

* cited by examiner

*Primary Examiner*—Emily Bernhardt
(74) *Attorney, Agent, or Firm*—Soma G. Simon; William T. King; Charles M. Kinzig

(57) ABSTRACT

Sulphonamide compounds according to formula (I) or pharmaceutically acceptable salts thereof:

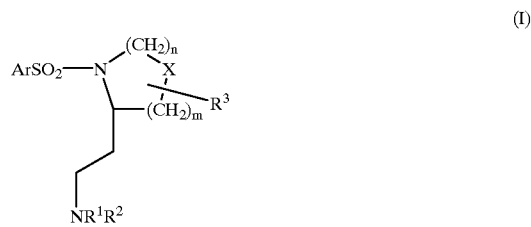

wherein:

Ar is naphthyl, phenyl or thienyl optionally substituted by one or more substituents selected from the group consisting of $C_{1-6}$ alkyl optionally substituted by $NR^7R^8$, $C_{2-6}$ alkenyl, $C_{2-6}$ alkynyl, $C_{1-6}$ alkylthio, cyano, nitro, halogen, $CF_3$, $C_2F_5$, $NR^7R^8$, $CONR^7R^8$, $NR^7COR^8$, $S(O)_pNR^7R^8$, CHO, $OCF_3$, $SCF_3$, $COR^9$, $CH_2OR^9$, $CO_2R^9$ or $OR^9$ where p is 1 or 2 and $R^7$, $R^8$ and $R^9$ are independently hydrogen or $C_{1-6}$ alkyl.

$R^1$ and $R^2$ are independently hydrogen or $C_{1-6}$alkyl or together with the nitrogen atom to which they are attached form a 5- to 7-membered heterocyclic ring optionally substituted by $C_{l-6}$alkyl and optionally containing a further heteroatom selected from nitrogen, sulphur or oxygen, the nitrogen atom being substituted by hydrogen, $C_{1-6}$ alkyl or $cycloC_{3-7}$alkyl;

$R^3$ is hydrogen or $C_{1-6}$ alkyl;

X is oxygen, sulphur or a bond;

n is 2 or 3; and m is 1 or 2;

are provided.

The present compounds are useful in the treatment of CNS disorders.

7 Claims, No Drawings

SULPHONAMIDE DERIVATIVES AND THEIR USE IN THE TREATMENT OF CNS DISORDERS

This invention relates to compounds having pharmacological activity, processes for their preparation, to compositions containing them and to their use in the treatment of CNS disorders.

EPA 0 021 580 and EPA 0 076 072 describe sulphonamide derivatives which are disclosed as having antiarrhythmic activity. A structurally distinct class of compounds has now been discovered, which have been found to have $5HT_7$ receptor antagonist activity. $5HT_7$ receptor antagonists are believed to be of potential use in the treatment of certain CNS disorders such as anxiety, depression, sleep disorders, and schizophrenia.

The present invention therefore provides, in a first aspect, a compound of formula (I) or a salt thereof:

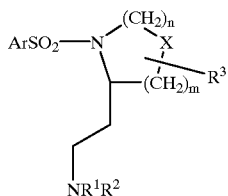
(I)

wherein:
Ar is an optionally substituted mono- or bicyclic aromatic or heteroaromatic ring;
$R^1$ and $R^2$ are independently hydrogen, $C_{1-6}$ alkyl, aryl$C_{1-6}$ alkyl or together with the nitrogen atom to which they are attached form an optionally substituted 5- to 7-membered heterocyclic ring optionally containing a further heteroatom selected from nitrogen, sulphur or oxygen, the nitrogen atom being substituted by hydrogen, $C_{1-6}$ alkyl, cyclo$C_{3-7}$ alkyl, or an optionally substituted aryl, heteroaryl or aryl$C_{1-6}$ alkyl group;
$R^3$ is hydrogen or $C_{1-6}$ alkyl;
X is oxygen, sulphur or a bond;
n is 2 or 3; and
m is 1 or 2.

$C_{1-6}$ Alkyl groups, whether alone or as part of another group, may be straight chain or branched.

Optional substituents for aromatic and heteroaromatic groups include $C_{1-6}$ alkyl optionally substituted by $NR^7R^8$, $C_{2-6}$ alkenyl, $C_{2-6}$ alkynyl, $C_{1-6}$ alkylthio, cyano, nitro, halogen, $CF_3$, $C_2F_5$, $NR^7R^8$, $CONR^7R^8$, $NR^7COR^8$, $S(O)_pNR^7R^8$, CHO, $OCF_3$, $SCF_3$, $COR^9$, $CH_2OR^9$, $CO_2R^9$ or $OR^9$ where p is 1 or 2 and $R^7$, $R^8$ and $R^9$ are independently hydrogen, $C_{1-6}$ alkyl, optionally substituted aryl or optionally substituted aryl$C_{1-6}$alkyl. More than one substituent can be present and in the case of multiple substituents these can be the same or different.

Suitably Ar is an optionally substituted mono- or bicyclic aromatic or heteroaromatic ring. Preferably Ar is an optionally substituted naphthyl, phenyl or thienyl group. Most preferably Ar is naphthyl, phenyl or thienyl substituted by one or more halogen, in particular 2,3-di-bromothienyl.

In $R^1$ and $R^2$ optional substituents for the heterocyclic rings include $C_{1-6}$ alkyl. Preferably $R^1$ and $R^2$ form an optionally substituted 5- to 7-membered heterocyclic ring, in particular an optionally substituted 6-membered ring. Most preferably $R^1$ and $R^2$ form a piperidine ring optionally substituted by one or two methyl groups, or $R^1$ and $R^2$ form a piperazine ring substituted on nitrogen with an optionally substituted aryl ring.

Preferably $R^3$ is hydrogen.
Preferably X is a bond.
Preferably n and m have values such that, together with X, they form part of a 5- or 6-membered ring.
Particular compounds of the invention include:

(±)-N-(1-Naphthylsulfonyl)-2-[1-(piperidinyl)ethyl]piperidine,
(±)-N-[(4,5-Dibromo)-thienyl-2-sulfonyl]-2-[1-(piperidinyl)ethyl]piperidine,
1-(2-[1-(Naphthalene-1-sulfonyl)-piperidin-2-yl]-ethyl)-4-pyrid-2-yl piperazine,
1-(2-[1-(Naphthalene-1-sulfonyl)-piperidin-2-yl]-ethyl)-4-phenyl piperazine,
(R)-4-Methyl-1-(2-(1-(3-methylphenylsulfonyl)-pyrrolidin-2-yl)-ethyl)-piperidine and pharmaceutically acceptable salts thereof.

The compounds of the formula (I) can form acid addition salts with acids, such as conventional pharmaceutically acceptable acids, for example maleic, hydrochloric, hydrobromic, phosphoric, acetic, fumaric, salicylic, citric, lactic, mandelic, tartaric and methanesulfonic.

Compounds of formula (I) may also form solvates such as hydrates, and the invention also extends to these forms. When referred to herein, it is understood that the term 'compound of formula (I)' also includes these forms.

Certain compounds of formula (I) are capable of existing in stereoisomeric forms including diastereomers and enantiomers and the invention extends to each of these stereoisomeric forms and to mixtures thereof including racemates. The different stereoisomeric forms may be separated one from the other by the usual methods, or any given isomer may be obtained by stereospecific or asymmetric synthesis. The invention also extends to any tautomeric forms and mixtures thereof.

The present invention also provides a process for the preparation of a compound of formula (I) or a pharmaceutically acceptable salt thereof, which process comprises
(a) the coupling of a compound of formula (II):

(II)

in which Ar is as defined in formula (I) and L is a leaving group with a compound of formula (III):

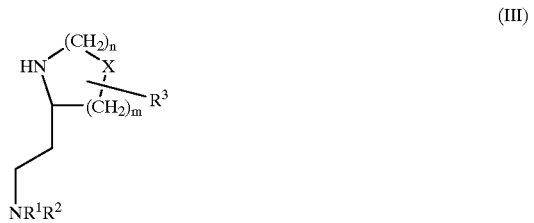
(III)

in which n, m, X, $R^1$, $R^2$ and $R^3$ are as defined in formula (I);

or (b) the coupling of a compound of formula (IV):

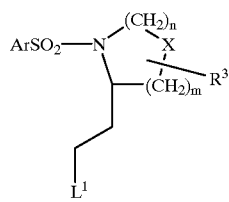

(IV)

in which Ar, n, m, X, and $R^3$ are as defined in formula (I) and $L^1$ is a leaving group with a compound of formula (V):

(V)

and optionally thereafter (a) or (b):
forming a pharmaceutically acceptable salt.

Suitable leaving groups L and $L^1$ include halogen in particular chloro. The reaction of a compounds of formulae (II) and (III) is preferably carried out in an inert solvent such as dichloromethane optionally in the presence of a base such as triethylamine.

Compounds of formulae (II) and (III) are commercially available or may be prepared according to known methods or analogous to known methods.

Pharmaceutically acceptable salts may be prepared conventionally by reaction with the appropriate acid or acid derivative.

Compounds of formula (I) and their pharmaceutically acceptable salts have $5HT_7$ receptor antagonist activity and are believed to be of potential use for the treatment or prophylaxis of CNS disorders such as anxiety, depression, sleep disorders, including instances of Circadian rhythym and schizophrenia.

Thus the invention also provides a compound of formula (I) or a pharmaceutically acceptable salt thereof, for use as a therapeutic substance, in particular in the treatment or prophylaxis of the above disorders.

The invention further provides a method of treatment or prophylaxis of the above disorders, in mammals including humans, which comprises administering to the sufferer a therapeutically effective amount of a compound of formula (I) or a pharmaceutically acceptable salt thereof.

In another aspect, the invention provides the use of a compound of formula (I) or a pharmaceutically acceptable salt thereof in the manufacture of a medicament for the treatment or prophylaxis of the above disorders.

The present invention also provides a pharmaceutical composition, which comprises a compound of formula (I) or a pharmaceutically acceptable salt thereof, and a pharmaceutically acceptable carrier.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusable solutions or suspensions or suppositories. Orally administrable compositions are generally preferred.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colourants.

For parenteral administration, fluid unit dosage forms are prepared utilising a compound of the invention or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilised by exposure to ethylene oxide before suspension in a sterile vehicle. Advantageously, a surfactant or wetting agent is included in the composition to facilitate uniform distribution of the compound.

The composition may contain from 0.1% to 99% by weight, preferably from 10 to 60% by weight, of the active material, depending on the method of administration.

The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 0.05 to 20.0 mg, for example 0.2 to 5 mg; and such unit doses may be administered more than once a day, for example two or three a day, so that the total daily dosage is in the range of about 0.5 to 100 mg; and such therapy may extend for a number of weeks or months.

When administered in accordance with the invention, no unacceptable toxicological effects are expected with the compounds of the invention.

The following Descriptions and Examples illustrate the preparation of compounds of the invention.

Description 1

2-(2-Chloroethyl)-1-(naphthalene-1-sulfonyl) piperidine (D1)

To a solution of 1-naphthalene sulfonyl chloride (26.64 g) in toluene (300 ml) was added 2-piperidine ethanol (8.99 g) and diisopropylethylamine (26.8 ml). The mixture was heated to reflux overnight. After cooling to room temperature the solvent was removed in vacuo and the residue chromatographed on silica eluting with 50% ethyl acetate and petroleum ether (bp 60–80). The title compound was isolated as an oil, which solidified on standing (12.5 g, 53%). $MH^+$ 338.

2-[1-(naphthalene-1-sulfonyl)-piperidin-2-yl]ethanol the more polar product was isolated as an oil (9.8 g, 44%).

Description 2

(R)-2-Hydroxymethyl-pyrrolidine-1-carboxylic acid tert-butyl ester (D2)

To a solution of (R)-2-pyrrolidine methanol (0.19 mol) and di-tert-butyl dicarbonate (0.2 mol) in THF (200 ml) and water (200 ml) was added potassium carbonate until the solution was basic (pH9). The reaction mixture was stirred at room temp. overnight, before partitioning between $CH_2Cl_2$ and $H_2O$. The organic phase was dried and concentrated and the residue purified by chromatography on silica gel (32.5 g, 84%) $MH^+$ 202.

Description 3

(R)-2-Methanesulfonyloxy-methyl-pyrrolidine-1-carboxylic acid, tert-butyl ester (D3)

To a solution of (R)-2-hydroxymethyl-pyrrolidine-1-carboxylic acid tert-butyl ester (D2) (0.32 mmol) in dichloromethane (750 ml) at 0° C. was added triethylamine (0.36 mol) and methane sulfonyl chloride (0.49 mol). Stirring was continued at 0° C. to room temperature for one hour. The reaction mixture was partitioned between $CH_2Cl_2$ and saturated aqueous $NaHCO_3$. The organic phase was dried and concentrated to afford the title compound (90 g, 100%) $MH^+$ 280.

Description 4

(R)-2-Cyanomethyl pyrrolidine-1-carboxylic acid, tert-butyl ester (D4)

To a solution of (R)-2-methanesulfonyloxy-methyl-pyrrolidine-1-carboxylic acid, tert-butyl ester (D3) (90 g, 0.32 mol) in DMF (1200 ml) was added sodium cyanide (24 g, 0.49 mol). Heated to 60° C. overnight. Reaction mixture was concentrated and partitioned between water and ether. The organic phase was dried and concentrated to give the title compound (18 g, 30%) (M-Boc) 110.

Description 5

(R)-2-[2-(4-Methyl-piperidin-1-yl)ethyl]pyrrolidone-1-carboxylic acid, tert-butyl ester (D5)

A solution of (R)-2-cyanomethyl pyrrolidine-1-carboxylic acid, tert-butyl ester (D4) (0.062 mol) and 4-methyl piperidine (0.12 mol) in ethanol (180 ml) was hydrogenated over $PtO_2$ at 35° C. at $3.44 \times 10^5$ $Nm^{-2}$ for 3 days. The reaction mixture was filtered and concentrated and the residue purified by chromatography on silica gel to afford the title compound (8.6 g, 47%) $MH^+$ 297.

Description 6

(R)-2-[2-(4-Methyl-piperidin-1-yl)ethyl]pyrrolidine (D6)

A solution of the protected amine, (R)-2-[2-(4-methyl-piperidin-1-yl)ethyl ]pyrrolidine-1-carboxylic acid, tert-butyl ester (D5) (3.0 g, 10 mmol) in trifluoroacetic acid (15 ml) and dichloromethane (50 ml) was heated to reflux for 18 hours. The reaction mixture was concentrated and the residue partitioned between $CH_2Cl_2$ and sat. aqueous $K_2CO_3$. The organic phase was dried and concentrated to afford the title compound (2.0 g, q) $MH^+$ 197.

Description 7

(S)-1-Benzyl-2-pyrrolidine acetonitrile (D7)

(S)-1-Benzyl-2-pyrrolidine methanol (10 g, 52 mmol) was converted to its mesylate derivative using methane sulfonyl chloride and triethylamine in dichloromethane. Treatment with sodium cyanaide in DMF afforded the title compound (8.9 g, 85%) $MH^+$ 201.

Description 8

(S)-Ethyl-1-benzyl-2-pyrrolidine ethanoate (D8)

(S)-1-Benzyl-2-pyrrolidine acetonitrile (D7) (4.9 g, 24 mmol) was converted to its ethyl ester by treatment with hydrogen chloride in ethanol (5.5 g, 90%) $MH^+$ 248.

Description 9

(S)-1-Benzyl-2-pyrrolidine ethanol (D9)

(S)-Ethyl-1-benzyl-2-pyrrolidine ethanoate (D8) (5.5 g, 22 mmol) was treated with lithium aluminium hydride to afford the title compound (4.9 g, 100%). $MH^+$ 206.

Description 10

(S)-1-Benzyl-2-(2-(4-methylpiperidine-1-yl)ethyl) pyrrolidine (D10)

(S)-1-Benzyl-2-pyrrolidine ethanol (D9) (4.9 g, 22 mmol) was converted to its mesylate using methanesulfonyl chloride and triethylamine in dichloromethane. Treatment with 4-methyl piperidine afforded the title compound (1.1 g, 17%) $MH^+$ 287.

Description 11

(R)-2-(2-Hydroxyethyl)pyrrolidine (D11).

(R)-2-Cyanomethyl pyrrolidine-1-carboxylic acid, tert-butyl ester (D4) was converted to (R)-pyrrolidin-2-yl-acetic acid by treatment with concentrated HCl at reflux. Subsequent reduction with lithium aluminium hydride afforded the title compound.

Description 12

3-Methylphenylsulfonic acid 2-[1-(3-methylphenylsulfonyl)pyrrolidin-2-yl]-ethyl ester (D12)

To a solution of (R)-2-(2-hydroxyethyl)pyrrolidine (D11) (530 mg, 4.6 mmol) in $CH_2Cl_2$ (50 ml) at 0° C. was added diisopropylethyl amine (13.8 mmol) followed by 3-methylphenyl sulfonyl chloride (13.8 mmol). Stirring was continued, allowing the solution to reach room temperature for 24 hrs. The reaction mixture was partitioned between $CH_2Cl_2$ and saturated aqueous sodium bicarbonate. The organic layer was dried ($Na_2SO_4$), filtered and concentrated in vacuo. The residue was purified by chromatography on silica gel to afford the title compound (530 mg, 27%). $MH^+$ 424

Description 13

2-Azepan-2-yl ethanol (D13)

The title compound was prepared according to the procedure outlined in U.S. Pat. No. 5,175,157.

Description 14

2-(2-Chloroethyl)-1-(naphthalene-1-sulfonyl)-azepene (D14)

The title compound was prepared in 56% yield according to the procedure outlined in D1 using 2-azepen-2-yl ethanol and 1-naphthalene sulfonyl chloride. $MH^+$ 352.

Description 15

3-(2-Chloroethyl)-4-(naphthalene-1-sulfonyl) thiomorpholine (D15)

The title compound (300 mg, 70%) was prepared according to the procedure outlined in D1 using 3-(2-hydroxyethyl) thiomorpholine and 1-naphthalenesulfonyl chloride.

EXAMPLE 1

(±)-N-(1-Naphthylsulfonyl)-2-[1-(piperidinyl)ethyl] piperidine (E1)

To a stirred solution of 2-[1-(piperidinyl)ethyl]piperidine (196 mg, 1 mmol) and triethylamine (0.14 ml, 1 mmol) in dichloromethane (10 ml) cooled by an ice bath, was added dropwise a solution of 1-naphthalene sulfonyl chloride (226 mg, 1 mmol) in dichloromethane. Stirring continued, allowing the solution to reach room temperature for 24 hours. The solution was washed thoroughly (10% NaOH), and brine, dried ($Na_2SO_4$) and concentrated in vacuo to afford a pale yellow oil (225 mg, 58%) $M^+$=387.

EXAMPLE 2

(±)-N-[(4,5-Dibromo)-thienyl-2-sulfonyl]-2-[1-(piperidinyl)ethyl]piperidine (E2)

To a stirred solution of 2-[1-(piperidinyl)ethyl]piperidine (290 mg, 1.47 mmol) and diisopropylethylamine (0.25 ml, 1.47 mmol) in dichloromethane cooled by an ice bath, was added dropwise a solution of 4,5-dibromothiophene-2-sulfonyl chloride (502 mg, 1.47 mmol) in dichloromethane (2 ml). The solution was allowed to warm to room temperature overnight, washed (sat. $NaHCO_3$, brine), dried ($Na_2SO_4$) and concentrated. The residue was purified by chromatography on silica, eluting with dichloromethane up to 2% methanol/dichloromethane to afford a yellow oil (370 mg, 50%). $M^+$=499, 501, 503

EXAMPLE 3

1-(2-[1-(Naphthalene-1-sulfonyl)-piperidin-2-yl]-ethyl)-4-pyrid-2-yl piperazine (E3)

To a solution of 2-(2-chloroethyl)-1-(naphthalene-1-sulfonyl)piperidine (D1) (250 mg) in acetonitrile (20 ml) was added sodium iodide (12 mg), potassium carbonate (108 mg) and 1-(2-pyridyl)piperazine (143 ul). The mixture was heated at reflux overnight. After cooling to room temperature the residue was chromatographed on silica eluting with 5% methanol in dichloromethane to afford the title compound as an oil (301 mg, 87%). Trituration with diethyl ether afforded a foam. $MH^+$ 465

EXAMPLE 4

1-(2-[1-(Naphthalene-1-sulfonyl)-piperidin-2-yl]-ethyl)-4-phenyl piperazine (E4)

The title compound (151 mg, 44%) was prepared according to the procedure outlined in Example 3. $MH^+$ 464

Examples E5–44 were also prepared using the procedure outlined in Example 3 using 2-(2-chloroethyl)-1-(naphthalene-1-sulfonyl)piperidine and an appropriate amine.

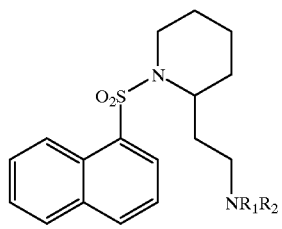

| Example | $NR^1R^2$ | $MH^+$ |
|---|---|---|
| 5 | Hexamethyleneimine | 401 |
| 6 | cis-2,6-Dimethylpiperidine | 415 |
| 7 | N-Methylbutylamine | 389 |

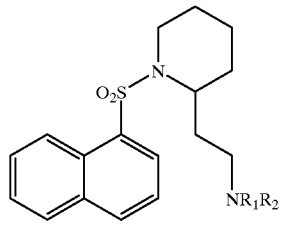

| Example | $NR^1R^2$ | $MH^+$ |
|---|---|---|
| 8 | N-Benzylmethylamine | 423 |
| 9 | Pyrrolidine | 373 |
| 10 | 1-(4-Benzyl)piperazine | 478 |
| 11 | N-Methylphenethylamine | 437 |
| 12 | Heptamethyleneimine | 415 |
| 13 | Morpholine | 389 |
| 14 | 3-Azabicyclo[3.2.2]nonane | 427 |
| 15 | 4-(o-Tolyl)piperazine | 477 |
| 16 | 4-Phenylpiperidine | 463 |
| 17 | 3-Methylpiperidine | 401 |
| 18 | 4-Methylpiperidine | 401 |
| 19 | 3,3-Dimethylpiperidine | 415 |
| 20 | 3,5-Dimethylpiperidine | 415 |
| 21 | Azepine | 449 |
| 22 | cis-Decahydroisoquinoline | 441 |
| 23 | Benzazepine | 449 |
| 24 | 4,4-Dimethylpiperidine | 415 |
| 25 | cis-Decahydroquinoline | 441 |
| 26 | 4-Benzylpiperidine | 477 |
| 27 | 4-Isopropylpiperidine | 429 |
| 28 | Isoindoline | 421 |
| 29 | 1,2,3,6-Tetrahydropyridine | 385 |
| 30 | 4-tert Butylpiperidine | 443 |
| 31 | 3,4-Dimethylpiperidine | 416 |
| 32 | 4-(4-Trifluoromethylphenyl)piperazine | 491 |
| 33 | 4-Phenethylpiperidine | 491 |
| 34 | 4-Phenyl-1,2,3,6-tetrahydropyridine | 461 |
| 35 | 4-Trifluoromethylpiperidine | 455 |
| 36 | 5-Bromoisoindole | 499/501 |
| 37 | 4-Bromoisoindole | 499/501 |
| 38 | 4-Phenpropylpiperidine | 506 |
| 39 | 5-Phenylisoindole | 497 |
| 40 | 4-Phenylisoindole | 497 |
| 41 | 4-Cyclohexylethylpiperidine | 497 |
| 42 | 2,4-Dimethylpiperidine | 415 |
| 43 | 1-(4-Acetyl)piperazine | 430 |
| 44 | 1-(4(3'-Trifluoromethylphenyl))piperazine | 532 |

EXAMPLE 45

(R)-2-[2-(4-Methyl-piperidin-1-yl)ethyl]-1-(naphthalene-1-sulfonyl)pyrrolidine (E45)

To a solution of (R)-2-[2-(4-Methyl-piperidin-1-yl)ethyl] pyrrolidine (D6) 1 mmol and -diisopropylethylamine (1 mmol) in dichloromethane (10 mL) at 0° C. was added 1-naphthalene sulfonyl chloride. Stirring was continued at room temp. for 12 hours. The solution was washed with 10% aqueous NaOH and brine, dried and concentrated. The residue was purified by chromatography on silica gel to afford the title compound ($MH^{30}$ 387).

Examples E46–87 were prepared using the procedure outlined in Example 45 using (R)-2-[2-(4-Methyl-piperidin-1-yl)ethyl]pyrrolidine (D6) and an appropriate aryl sulfonyl chloride.

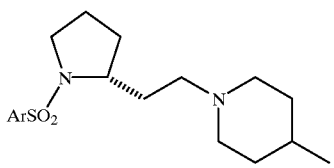

| Example | Ar | MH+ |
|---|---|---|
| 46 | 4,5-Dibromo-2-thiophene | 499/501/503 |
| 47 | 3,4-Dichlorophenyl | 405/407 |
| 48 | 3,4-Dibromophenyl | 493/495/497 |
| 49 | 3-Methyl phenyl | 351 |
| 50 | 4-Chloro-3-vinylphenyl | 397/399 |
| 51 | 3-Bromophenyl | 415/417 |
| 52 | 3-(2-Methylphenyl)phenyl | 427 |
| 53 | 4-Trifluoromethoxyphenyl | 421 |
| 54 | 8-Quinolyl | 388 |
| 55 | 4-Bromo-2-trifluoromethoxyphenyl | 499/501 |
| 56 | 2,5-bis-(1,1,1-Trifluoroethoxy)phenyl | 533 |
| 57 | 2-Trifluoromethoxyphenyl | 421 |
| 58 | 2'-(Methoxycarbonyl)phenyl | 395 |
| 59 | 3-(Isopropyloxymethyl) | 409 |
| 60 | 3-(4-Chlorophenyloxymethyl) | 477/479 |
| 61 | 3-Hydroxymethylphenyl | 367 |
| 62 | 8-Chloro-1-naphthyl | 421/423 |
| 63 | 3-Benzyloxyphenyl | 443 |
| 64 | 3-(4'-Bromobenzyloxy)phenyl | 521/523 |
| 65 | 3-Hydroxyphenyl | 353 |
| 66 | 3-(2-Naphthyl)phenyl | 463 |
| 67 | 3-(1-Naphthyl)phenyl | 463 |
| 68 | 3-(4-Methoxyphenyl)phenyl | 443 |
| 69 | 3-(3,5-bisTrifluoromethylphenyl)phenyl | 549 |
| 70 | 3-(3-Trifluoromethylphenyl)phenyl | 481 |
| 71 | 3-(2,4,6-Trimethylphenyl)phenyl | 455 |
| 72 | 3-(2-Trifluoromethylphenyl)phenyl | 481 |
| 73 | 5-Bromo-4-methoxyphenyl | 445/447 |
| 74 | 3-Chloro-2-methylphenyl | 385/387 |
| 75 | 4-Chloro-2,5-dimethylphenyl | 399/401 |
| 76 | 2-Cyanophenyl | 362 |
| 77 | 2,5-Dichlorophenyl | 405/407/409 |
| 78 | 5-Fluoro-2-methyl | 369 |
| 79 | 2,3-Dichlorophenyl | 405/407 |
| 80 | 3-(4-Bromobenzyloxy)phenyl | 521/523 |
| 81 | 3-Trifluoromethane sulfonyloxyphenyl | 485 |
| 82 | 3-Acetoxyphenyl | 395 |
| 83 | 3-Methoxyphenyl | 367 |
| 84 | 3-(3-Chlorophenyl)phenyl | 447/449 |
| 85 | 3-(3-Methoxyphenyl)phenyl | 443 |
| 86 | 7-(2-Trifluoroacetyl-1,2,3,4-tetrahydoisoquinoline) | 488 |
| 87 | 7-(1,2,3,4-Tetrahydroisoquinoline) | 392 |

EXAMPLE 88

(S)-2-[2-Methylpiperidine-1-yl)ethyl)-1-(naphthalene-1-sulfonyl)pyrrolidine (E88)

Hydrogenation of (S)-1-Benzyl-2-(2-(4-methylpiperidine-1-yl)ethyl)pyrrolidine (D10, 300 mg, 1.05 mmol) over palladium hydroxide and treatment of the debenzylated product with 1-naphthalene sulfonyl chloride afforded the title compound (80 mg, 20%) MH+ 387.

EXAMPLES 89–102

Were Prepared by the Following Generic Procedure

To a suspension of 3-Methylphenylsulfonic acid 2-[1-(3-methylphenylsulfonyl)pyrrolidin-2-yl]-ethyl ester (D12) (1 mmol), potassium carbonate (1 mmol) and sodium iodide (0.1 mmol) in acetone (20 ml) was added a solution of the amine (1 mmol) in acetone (1 ml). The reaction mixtue was heated to reflux for 14 hrs. After cooling to room temp. the solvent was removed in vacuo and the residue purified by chromatography on silica gel.

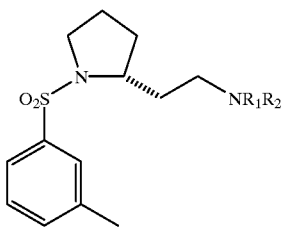

| Example | NR¹R² | MH+ |
|---|---|---|
| 89 | Phenethylamine | 373 |
| 90 | 8-(3-Methyl-8-azabicyclo[3.2.1]octane | 377 |
| 91 | 8-(3-Hydroxy-8-azabicyclo[3.2.1]octane | 379 |
| 92 | 2-(2-Azabicyclo[3.3.1]nonane) | 377 |
| 93 | 4-Methylpiperazine | 352 |
| 94 | 4-Acetylpiperazine | 380 |
| 95 | 4-Ethoxypiperidine | 381 |
| 96 | Thiomorpholine | 355 |
| 97 | Isopropylamine | 311 |
| 98 | 3-Methylmorpholine | 353 |
| 99 | 3-Oxo-4-methylpiperazine | 366 |
| 100 | 4-Acetyl-3-methylpiperazine | 394 |
| 101 | 3-Methylpiperazine | 352 |
| 102 | 1-(2-Methylhexahydropyridazine) | 352 |

EXAMPLE 103

2-[2-(4-Methyl-piperidin-1-yl)ethyl]-1-(naphthalene-1-sulfonyl)-azepene (E103)

The title compound was prepared in 77% yield according to the procedure outlined in Examples 5–44 using 4-methyl piperidine and 2-(2-chloroethyl)-1-(naphthalene-1-sulfonyl)-azepene (D14). MH+ 415.

EXAMPLE 104

2-(2-[1-(Naphthalene-1-sulfonyl)-azepene-2-yl]ethyl)-1,2,3,4-tetrahydroisoquinoline (E104)

The title compound was prepared in 57% yield according to the procedure outlined in Examples 5–44 using 1,2,3,4 tetrahydroisoquinoline and 2-(2-chloroethyl)-1-(naphthalene-1-sulfonyl)-azepene (D14). MH+ 449.

EXAMPLE 105

3-(2-(4-Methylpiperidin-1-yl)ethyl)-4-(naphthalene-1-sulfonyl)thiomorpholine (E105)

The title compound (250 mg, 63%) was prepared according to the procedure outlined in Examples 5–44 using 3-(2-chloroethyl)-4-(naphthalene-1-sulfonyl) thiomorpholine and 4-methylpiperidine. MH+ 419.

Pharmacological Data

[$^3$H]-5-Carboxamidotryptamine binding to human 5-HT$_7$ receptor clones expressed in 293 cells in vitro The affinity of test drugs for the 5-HT$_7$ receptor binding site can be determined by assessing their ability to displace [$^3$H]-5-carboxamidotryptamine from 5-HT$_7$ receptor clones expressed in 293 cells (To et al., 1995 and Sleight et al., 1995).

The cells suspension (400 μl) was incubated with [$^3$H]-5-carboxamido-tryptamine (0.5 nM) in Tris HCl buffer (pH 7.4) at 37° C. for 45 mins. Non-specific binding was measured in the presence of 5-hydroxytryptamine ($10^{-6}$M). Ten concentrations of test drug ($10^{-11}$ to $10^{-5}$M final concentration) were added in a volume of 50 ul. The total assay volume was 500 µl. Incubation was stopped by rapid filtration using a Tomtec cell harvester and radioactivity measured by scintillation counting on a Packard Topcount. The $IC_{50}$ values and pKi values were calculated by INFLEXION, a non-linear iterative curve fitting programme based in EXCEL (Bowen and Jerman, 1994).

Bowen, W. and Jerman, J. (1994). Br. J. Pharmacol.,112, 440P.

Sleight, A. J., Carolo, C., Petit, N., Zweingelstein, C. and Bourson, A. (1995). Mol. Pharmacol.,47, 99.

To, Z. P., Bonhaus, D. W., Eglen, R. M. and Jakeman, L. B. (1995). Br. J. Pharmacol.,15, 107.

All the compounds of examples 1 to 105 showed activity in the above test.

What is claimed is:

1. A compound of formula (I) or a pharmaceutically acceptable salt thereof:

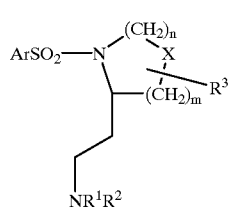

(I)

wherein:
Ar is naphthyl, or phenyl optionally substituted by one or more substituents selected from the group consisting of $C_{1-6}$ alkyl optionally substituted by $NR^7R^8$, $C_{2-6}$ alkenyl, $C_{2-6}$ alkynyl, $C_{1-6}$ alkylthio, cyano, nitro, halogen, $CF_3$, $C_2F_5$, $NR^7R^8$, $CONR^7R^8$, $NR^7COR^8$, $S(O)_pNR^7R^8$, CHO, $OCF_3$, $SCF_3$, $COR^9$, $CH_2OR^9$, $CO_2R^9$ or $OR^9$ where p is 1 or 2 and $R^7$, $R^8$ and $R^9$ are independently hydrogen or $C_{1-6}$ alkyl;

$NR^1R^2$ forms a piperidine ring optionally substituted by one or two $C_{1-6}$ alkyl groups or a piperazine ring optionally substituted on nitrogen with a substituent selected from the group consisting of $C_{1-6}$ alkyl, $C_{3-7}$ cycloalkyl, phenyl and phenyl($C_{1-6}$)alkyl;

$R^3$ is hydrogen or $C_{1-6}$ alkyl;

X is a bond;

n is 2; and m is 1.

2. A compound according to claim 1 which is:
(R)-4-Methyl-1-(2-(1-(3-methylphenylsulfonyl)-pyrrolidin-2-yl)-ethyl)-piperidine
or a pharmaceutically acceptable salt thereof.

3. A compound according to claim 1 which is (((R)-3-(2-(2-(4-methyl-piperidin-1-yl)ethyl)-pyrrolidine-1-sulfonyl)-phenol)).

4. A pharmaceutical composition which comprises a compound according to claim 1 and a pharmaceutically acceptable carrier or excipient.

5. A method of treating anxiety and/or depression comprising administering a compound safe and pharmaceutically effective amount of according to claim 1.

6. A method of treatment of a CNS disorder selected from anxiety, depression, and sleep disorders comprising administering to a subject in need of treatment a safe and pharmaceutically effective amount of a compound according to claim 1.

7. A process for the preparation of a compound of formula (I) according to claim 1 or a pharmaceutically acceptable salt thereof, which process comprises:

(a) the coupling of a compound of formula (II):

$$ArSO_2L \qquad (II)$$

in which Ar is as defined in formula (I) and L is a leaving group with a compound of formula (III):

(III)

in which n, m, X, $R^1$, $R^2$ and $R^3$ are as defined in formula (I);

or (b) the coupling of a compound of formula (IV):

(IV)

in which Ar, n, m, X, and $R^3$ are as defined in formula (I) and $L^1$ is a leaving group with a compound of formula (V):

$$HNR^1R^2 \qquad (V)$$

and optionally thereafter (a) or (b):
forming a pharmaceutically acceptable salt.

* * * * *